Figure 1:
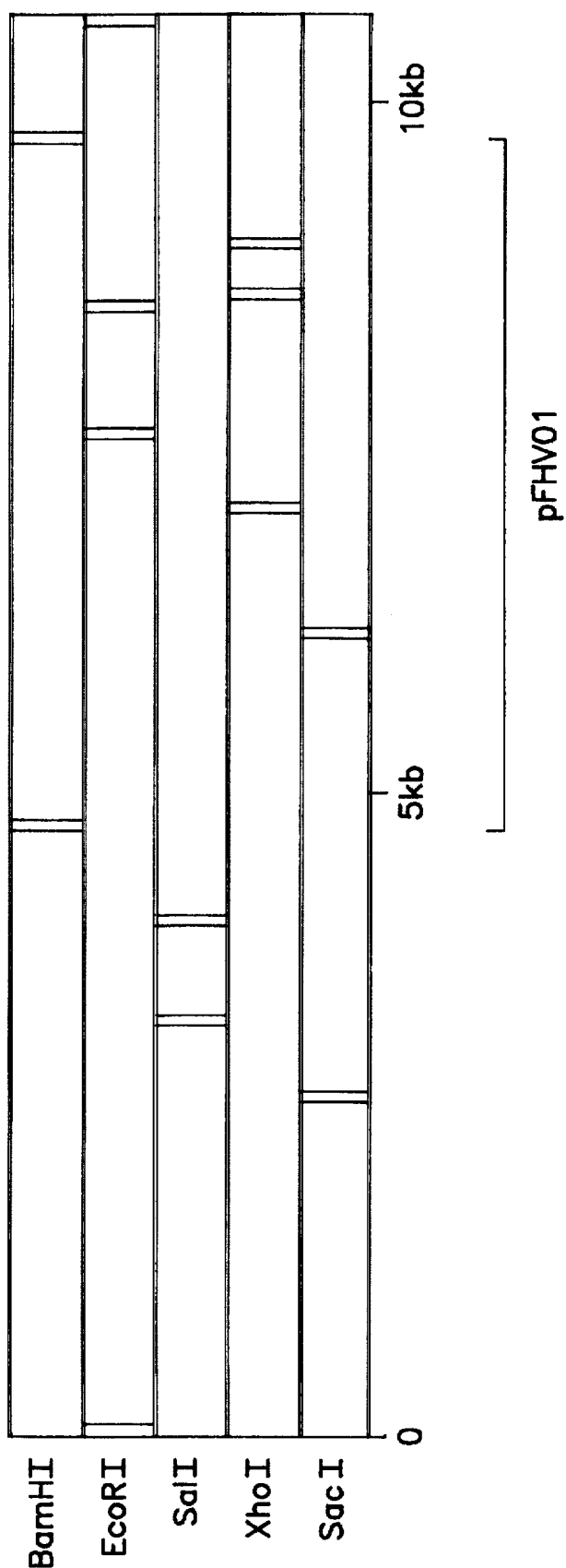

US005783192A

United States Patent [19]

Willemse et al.

[11] Patent Number: 5,783,192
[45] Date of Patent: Jul. 21, 1998

[54] RECOMBINANT FELINE HERPESVIRUS VACCINE

[75] Inventors: Martha Jacoba Willemse, Nijmegen; Paulus Jacobus Antonius Sondermeijer, Boxmeer, both of Netherlands

[73] Assignee: Akzo Nobel N.V., Arnhem, Netherlands

[21] Appl. No.: 664,894

[22] Filed: Jul. 17, 1996

Related U.S. Application Data

[60] Continuation of Ser. No. 453,527, May 30, 1995, abandoned, which is a division of Ser. No. 83,849, Jun. 28, 1993.

[30] Foreign Application Priority Data

Jun. 26, 1992 [EP] European Pat. Off. ............ 92201898

[51] Int. Cl.$^6$ ................... A61K 39/12; A61K 39/245
[52] U.S. Cl. .................. 424/199.1; 424/184.1; 424/185.1; 424/229.1; 424/205.1; 435/172.3; 435/69.3; 435/236; 435/240.1
[58] Field of Search ............... 424/185.1, 199.1, 424/229.1, 184.1, 205.1, 819; 435/69.1, 69.3, 172.3, 235.1, 236, 240.1, 320.1

[56] References Cited

FOREIGN PATENT DOCUMENTS

| 8704463 | 7/1987 | WIPO. |
| 9001547 | 2/1990 | WIPO. |

OTHER PUBLICATIONS

P.A. Rota et al., "Physical Characterization of the Genome of Feline Herpes–virus–1," Virology, vol. 154, No. 1, pp. 168–179, Oct. 15, 1986, New York, USA.

G.E. Cole et al., "Recombinant Feline Herpesvirus Expressing Feline Leukimia Virus Envelope and Gag Proteins," Journal of Virology, vol. 64 No. 10, pp. 4930–4938, Oct. 1990.

L. Nicholson et al., "The Nucleotide Sequnece of the Equine Herpesvirus 4 gC Gene Homologue," Virology, vol. 179, No. 1, pp. 378–387, Nov. 1990, NY.

G.P. Allen et al., "Characterization of an Equine Herpesvirus Type 1 Gene Encoding a glycoprotein (gp13) with Homology to HSV Glycoprotein C," Journal of Virology, vol. 62, No. 8, pp. 2850–2858, Aug. 1988.

*Primary Examiner*—Christine M. Nucker
*Assistant Examiner*—Laurie Scheiner
*Attorney, Agent, or Firm*—Mary E. Gormley

[57] ABSTRACT

The present invention is concerned with a Feline herpesvirus (FHV) mutant comprising a heterologous gene introduced into an insertion-region of the FHV genome.

The invention also relates to a vector vaccine comprising such an FHV mutant which expresses a heterologous polypeptide derived from a feline pathogen and induces an adequate immune response in an inoculated host against both FHV and the feline pathogen.

13 Claims, 5 Drawing Sheets

RECOMBINANT FELINE HERPESVIRUS VACCINE

This is a continuation of application U.S. Ser. No. 08/453,527, filed May 30, 1995, now abandoned, which is a divisional of U.S. Ser. No. 08/083,849, filed Jun. 28, 1993.

The present invention is concerned with a feline herpesvirus (FHV) mutant comprising a mutation in a region of the FHV genome, a nucleic acid sequence comprising an FHV insertion-region, a nucleic acid sequence comprising a heterologous nucleic acid sequence flanked by DNA derived from the insertion-region, a recombinant DNA molecule comprising such nucleic acid sequences, a cell culture infected with an FHV mutant, as well as vaccine comprising the FHV mutant.

BACKGROUND OF THE INVENTION

One of the major clinical problems in diseases of Felidae is associated with respiratory tract infections. The great majority of these cases are caused by either feline herpesvirus 1 (FHV) or feline calicivirus.

FHV is the causative agent of feline viral rhinotracheitis in cats. In kittens, FHV infection can generalize resulting in mortality rates of up to 50%. The disease is common and is found world-wide and is characterized by sneezing, depression, and ocular and nasal discharge.

The FHV is a member of the family Herpes-viridae, subfamily α-herpesvirus. The genome is about 126 kbp in length and is composed of a unique long ($U_L$) region of about 99 kbp and a short region of 27 kbp comprising an unique short ($U_S$) region of about 9 kbp flanked by inverted repeats of about 8 kbp (Grail et al., Arch. Virol. 116, 209–220, 1991).

Because of the prevalence and seriousness of FHV infection feline viral rhinotracheitis vaccines comprising modified live or killed FHV have been developed and have resulted in a successful reduction of the incidence of the disease.

In addition to FHV infection, cats are also susceptible to infection by various other pathogens, such as feline leukemia virus (FeLV), feline calicivirus, feline immunodeficiency virus (FIV), feline coronavirus and feline Chlamydia. At present, in general, cats can be protected against infection by these pathogenic micro-organisms with live or inactivated vaccines or by vaccines derived from subunits of the relevant pathogens.

However, these types of vaccines may suffer from a number of drawbacks. Using attenuated live vaccines always involves the risk of inoculating animals with inadequately attenuated pathogenic micro-organisms. In addition the attenuated pathogens may revert to a virulent state resulting in disease of the inoculated animals and the possible spread of the pathogen to other animals.

Inactivated vaccines generally induce only a low level of immunity, requiring repeated immunizations. Furthermore, the neutralization inducing antigenic determinants of the pathogens may become altered by the inactivation treatment, decreasing the protective potency of the vaccine.

Moreover, a problem with combined live viral vaccines is the mutual influence of the antigenic components resulting in a decrease of the potency of one or more of the constituting components.

A recombinant or naturally derived subunit vaccine also displays a number of disadvantages. First, a polypeptide subunit presented to the immune system as a non-replicating structure often does not elicit long-lasting immunity requiring also the presence of an adjuvant. Secondly, a presentation as a replicating structure can elicit immunity more efficiently than can a presentation as a subunit structure.

Furthermore, with currently administered live attenuated or inactivated FHV vaccines it is not possible to determine whether a specific animal is a carrier of an FHV field virus or whether the animal was vaccinated. Hence, it is important to be able to identify animals vaccinated with an FHV vaccine or infected with a field virus so as to be able to take appropriate measures to reduce spreading of a virulent field virus.

It is an object of the present invention to provide an FHV mutant which can be used not only for the preparation of a vaccine against feline viral rhinotracheitis but also against other infectious diseases of Felidae, which obviates any potential risk associated with the use of a live attenuated pathogen as a vaccine, which stimulates both the humoral and cellular immune system in a potent way without the explicit need of an adjuvant and which offers the possibility of a multivalent vaccine without the risk of adverse mutual interference of different antigenic components.

An other object of the present invention is to provide an FHV vaccine virus which is distinguishable from any field strain or any other FHV vaccine virus.

SUMMARY OF THE INVENTION

The present invention provides an FHV mutant comprising a mutation in the FHV genome in a region defined by the DNA sequence of the open reading frame encoding a polypeptide shown in SEQ ID NO: 2 and flanking intergenic sequences thereof.

A mutation is understood to be a change of the genetic information in the above-mentioned region with respect to the genetic information present in this region of the genome of naturally occurring FHV. The mutation is, for example, a nucleic acid substitution, deletion, insertion or inversion, or a combination thereof resulting in an FHV mutant which fails to produce any antigenic or functional polypeptide shown in SEQ ID NO: 2.

Preferably, the mutation introduced into the defined region of the FHV-genome is a deletion or insertion.

DETAILED DESCRIPTION OF THE INVENTION

In particular the present invention provides a recombinant FHV mutant characterized in that it comprises a heterologous nucleic acid sequence, said nucleic acid sequence being introduced in the region of the FHV genome defined by the DNA sequence of the open reading frame (ORF) encoding a polypeptide shown in SEQ ID NO: 2 and flanking intergenic sequences thereof.

The FHV mutant according to the present invention can be derived from any FHV strain, e.g. strain G2620 (commercially available from Intervet International B.V., the Netherlands), C-27 (ATCC VR-636), FVRm (ATCC VR-814), FVRm vaccine (ATCC VR-815) or F2.

BRIEF DESCRIPTION OF THE DRAWINGS

FIG. 1

Restriction map of the 10.9 kb DNA insert from λFHV02. The position of this fragment in the viral genome was mapped near the left end of the unique long segment. Subcloning of the 5.1 kb BamHI fragment resulted in pFHV01.

FIG. 2

A—Map of plasmid pFHV01 containing the 5.1 kb BamHI restriction fragment from λFHV02 subcloned in pGEM3Z.

B—Map of plasmid pFHV04 containing a 4.0 kb β-galactosidase expression cassette inserted at the unique BglII restriction site of pFHV01.

FIG. 3

A—Restriction map of pFHV24. This construct was derived from pFHV02 by eliminating excess sequences flanking the insertion region as defined in SEQ ID: 1. The position of the open reading frame (ORF) as defined in SEQ ID: 1 is shown at the top.

B—Restriction map of plasmid pFHV28, containing the LTR promotor with multiple cloning site inserted at the unique BglII site of pFHV24. This vector enables the integration of foreign genes into the genome of FHV by means of in vivo recombination.

FIG. 4

Restriction map of pFHV29 which contains the gene encoding the envelope protein from FeLV inserted at the BglII site from pFHV28 downstream of the LTR promotor.

FIG. 5

Restriction map of pFHV37 which contains the gene encoding the envelope protein from FIV inserted at the BglII site from pFHV28 downstream of the LTR promotor.

The term "recombinant FHV mutant" as used herein denotes infective virus which has been genetically modified by incorporation into the virus genome of a heterologous nucleic acid sequence, i.e. DNA which comprises a nucleic acid sequence not identical to the nucleic acid sequence of a gene naturally present in FHV.

On infection of a cell by the recombinant FHV mutant, it may express the heterologous gene in the form of a heterologous polypeptide.

The term "polypeptide" refers to a molecular chain of amino acids, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

The prerequisite for a useful (recombinant) FHV mutant is that the mutation such as an inserted heterologous nucleic acid sequence is incorporated in a permissive position or region of the genomic FHV sequence, i.e. a position or region which can be used for the incorporation of the mutation without disrupting essential functions of FHV such as those necessary for infection or replication. In the case of the insertion of a heterologous nucleic acid sequence such a region is called an insertion-region.

Until now little is known about the localization of genes on the FHV genome. Rota et al. (Virology 154, 168–179, 1986) and Grail et al. (Arch. Virol. 116, 209–220, 1991) disclosed physical maps of the FHV genome. Nunberg et al. (J. Virology 63, 3240–3249, 1989) and Cole et al. (J. Virology 64, 4930–4938, 1990) identified the thymidine kinase (TK) gene and mapped this gene in the SalI-A restriction fragment (Rota et al., supra) of the FHV genome. Subsequently, several recombinant FHV strains were constructed in which FeLV env and gag genes have been inserted within the FHV TK gene.

The (insertion-)region referred to in the present invention has not been identified previously within the FHV genome. Surprisingly, it has been found that a mutation such as the incorporation of heterologous DNA is allowable in this region without disrupting essential functions of the FHV.

Even more unexpected, it has been found that the introduction of a mutation into the region defined above significantly reduces the virulence of the live FHV mutant without affecting the protective properties of the FHV mutant. This finding has offered the possibility to obtain an attenuated FHV mutant, e.g. by introducing a deletion or insertion into the region defined above, which mutant can be administered safely to the animals to be vaccinated in a live form, even via the oro-nasal route.

The (insertion-)region used to introduce a mutation such as the insertion of a heterologous DNA sequence in order to prepare a FHV mutant according to the invention is located within a 10.9 kb restriction fragment generated by partial digestion of genomic FHV DNA with the enzyme Sau3A.

Said fragment is analyzed in detail by restriction enzyme mapping and essentially corresponds to a region within the $U_L$ segment of the viral genome between map unit 0.08 and 0.17 on the map of Grail et al. (1991, supra).

The (insertion-)region disclosed herein is located within a SalI fragment and comprises the DNA sequence encoding a polypeptide of 193 amino acids as shown in SEQ ID NO: 2 as well as its upstream and downstream flanking intergenic sequences. These upstream and downstream flanking intergenic sequence do not form part of an ORF or protein encoding DNA sequence, or do not comprise sequences regulating the replication of the virus. Said flanking sequences extend in the upstream and downstream direction up to the start or end of the nearest open reading frame.

Preferably, the upstream and downstream flanking intergenic sequences are about 252 and 173 bp in length, respectively.

It is a preferred object of the present invention to provide a (recombinant) FHV mutant that contains a mutation, such as a heterologous nucleic acid sequence into the (insertion-) region essentially defined by the DNA sequence shown in SEQ ID NO: 1.

In particular, a mutation such as a heterologous DNA sequence is incorporated into the FHV DNA sequence encoding the 193 amino acid long polypeptide defined by the amino acid sequence shown in SEQ ID NO: 2, and more specifically by its DNA sequence corresponding to the nucleotide position 253–834 shown in SEQ ID NO: 1, the unique BglII restriction site at nucleotide position 576 being the most favourable site for insertion of the heterologous DNA.

It will be understood that for the DNA sequence of the FHV genome, natural variations can exist between individual FHV viruses. These variations may result in deletions, substitutions, insertions, inversions or additions of one or more nucleotides. These FHV variants may encode a corresponding ORF that differs from the ORF disclosed herein. The DNA sequence encoding such variant ORFs can be located by several methods, including hybridization with the DNA sequence provided in SEQ ID NO: 1, or comparison of the physical map to locate analogous regions encoding said ORF. Therefore, the present invention provides an (insertion-)region obtainable from any strain of FHV.

Moreover, the potential exists to use genetic engineering technology to bring about above-mentioned variations resulting in a DNA sequence related to the DNA sequence of the (insertion-)region defined above. It is clear that a (recombinant) FHV mutant comprising a mutation, such as an inserted heterologous gene incorporated into an (insertion-)region located within the FHV genome characterized by such a related DNA sequence is also included within the scope of the present invention.

Furthermore, as the (insertion-)region identified according to the present invention does not display essential functions, said region can be deleted partially or completely, whereafter a heterologous gene can be incorporated into said deletion if desired.

In summary, the (insertion-)region essentially defined above characterizes the localization of a region within the FHV genome which can be used to incorporate a heterologous nucleic acid sequence, if desired after deleting DNA sequences from this region, or can be used to introduce other mutations, in particular a deletion in said region.

The heterologous nucleic acid sequence to be incorporated into the FHV genome according to the present invention can be derived from any source, e.g. viral, prokaryotic, eukaryotic or synthetic. Said nucleic acid sequence can be derived from a pathogen, preferably a feline pathogen, which after insertion into the FHV genome can be applied to induce immunity against disease.

Preferably nucleic acid sequences encoding a polypeptide of feline leukemia virus, feline immuno-deficiency virus, feline calicivirus, feline parvo-virus, feline coronavirus and feline Chlamydia are contemplated for incorporation into the insertion-region of the FHV genome.

Furthermore, nucleic acid sequences encoding polypeptides for pharmaceutical or diagnostic applications, in particular immuno-modulators such as lymphokines, interferons or cytokines, may be incorporated into said insertion-region.

An essential requirement for the expression of the heterologous nucleic acid sequence in a recombinant FHV mutant is an adequate promotor operably linked to the heterologous nucleic acid sequence. It is obvious to those skilled in the art that the choice of a promotor extends to any eukaryotic, prokaryotic or viral promotor capable of directing gene transcription in cells infected by the recombinant FHV, e.g. promotors of the retroviral long terminal repeat (Gorman et al., Proc. Natl. Acad. Sci. USA 79, 6777–6781, 1982), the SV40 promotor (Mulligan and Berg, Science 209, 1422–1427, 1980) or the cytomegalovirus immediate early promotor (Schaffner et al., Cell 41, 521–530, 1985).

In case a deletion mutant according to the invention is desired, either partial or complete deletion of the region from the viral genome identified above can be achieved by the technique of in vivo homologous recombination.

First, a DNA fragment comprising part of the unique long sequence as defined in SEQ ID No.: 1 and flanked by at least 100 nucleotides on either site, can be subcloned into a convenient plasmid vehicle.

The deletion to be introduced in the described region can be made in this plasmid by a restriction digest with one or more enzymes of which the sites are correctly positioned in or near the open reading frame. Recircularization of the remaining plasmid molecule would result in a derivative lacking at least part of the coding sequence present within the newly identified region. Alternatively, progressive deletions can be introduced either in one or two directions starting from within a restriction site present within the sequence of the open reading frame. Enzymes such as BalI or enonuclease III can be used for this purpose. Recircularized plasmid molecules are transformed into E. coli cells and individual colonies are analyzed by restriction mapping in order to determine the size of the deletion introduced into the specified region. An accurate positioning of the deletion can be obtained by sequence analysis. The plasmid containing a defined deletion can be cotransfected with FHV viral DNA into cultured feline cells. After in vivo recombination has occured, the deletion will be introduced at the correct position within the described region of the viral genome. Recombinants among the viral progeny can be identified for example by means of 15 to 20 bases long synthetic oligomer which hybridizes specifically to the nucleotide sequence which is generated at the junction where the deletion or originally was introduced.

The technique of in vivo homologous recombination can be used to introduce the heterologous nucleic acid sequence into the FHV genome. This is accomplished by first constructing a recombinant DNA molecule for recombination with FHV genomic DNA. Such a molecule may be derived from any suitable plasmid, cosmid or phage, plasmids being most preferred, and contains a heterologous nucleic acid sequence, if desired operably linked to a promotor. Said nucleic acid sequence and promotor are introduced into a fragment of genomic FHV DNA containing insertion-region sequences as defined herein subcloned in the recombinant DNA molecule. The insertion-region sequences which flank the heterologous nucleic acid sequence should be of appropriate length, e.g. 50–3000 bp, as to allow in vivo homologous recombination with the viral FHV genome to occur. If desired, a construct can be made which contains two or more different heterologous nucleic acid sequences derived from the same or different pathogens said sequences being flanked by insertion-region sequences of FHV defined herein. Such a recombinant DNA molecule can be employed to produce recombinant FHV which expresses two or more different antigenic polypeptides to provide a multivalent vaccine.

Secondly, cells, e.g. feline kidney cells (CRFK) or feline embryo cells can be transfected with FHV DNA in the presence of the recombinant DNA molecule containing the heterologous nucleic acid sequence flanked by appropriate FHV sequences whereby recombination occurs between the insertion-region sequences in the recombinant DNA molecule and the insertion-region sequences in the FHV genome. Recombination can also be brought about by transfecting the infected cells with a nucleic acid sequence containing the heterologous nucleic acid sequence flanked by appropriate flanking insertion-region sequences without plasmid sequences. Recombinant viral progeny is thereafter produced in cell culture and can be selected for example genotypically or phenotypically, e.g. by hybridization, detecting enzyme activity encoded by a gene co-integrated along with the heterologous nucleic acid sequence or detecting the antigenic heterologous polypeptide expressed by the recombinant FHV immunologically. Recombinant virus can also be selected positively based on resistance to compounds such as neomycine, gentamycine or mycophenolic acid. The selected recombinant FHV can be cultured on a large scale in cell culture whereafter recombinant FHV containing material or heterologous polypeptides expressed by said FHV can be collected therefrom.

A live FHV mutant according to the present invention, and in particular a live recombinant FHV expressing one or more different heterologous polypeptides of specific pathogens, can be used to vaccinate animals, particularly domestic and non-domestic cats or canine species. Vaccination with such a live vector vaccine is preferably followed by replication of the recombinant FHV within the inoculated host, expressing in vivo the heterologous polypeptide along with the FHV polypeptides. The polypeptides expressed in the inoculated host will then elicit an immune response against both FHV and the specific pathogen. If the heterologous polypeptide derived from the specific pathogen can stimulate a protective immune response, then the animal inoculated with a recombinant FHV mutant according to the invention will be immune to subsequent infection by that pathogen as well as to infection by FHV. Thus, a heterologous nucleic acid sequence incorporated into the insertion-region of the FHV genome according to the invention may be continuously expressed in vivo, providing a solid, safe and longlasting immunity to a pathogen.

A recombinant FHV mutant according to the invention containing and expressing one or more different heterologous polypeptides can serve as a monovalent or multivalent vaccine.

For the preparation of a live vaccine the recombinant FHV mutant according to the present invention can be grown on a cell culture of feline origin. The viruses thus grown can be harvested by collecting the tissue cell culture fluids and/or cells. The live vaccine may be prepared in the form of a suspension or may be lyophilized.

In addition to an immunogenically effective amount of the recombinant FHV the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol $F^{(R)}$ or Marcol $52^{(R)}$, saponins or vitamin-E solubilisate.

The useful dosage to be administered will vary depending on the age, weight and mode of administration. A suitable dosage can be for example about $10^{4.5}$ pfu/animal.

An FHV mutant according to the invention can also be used to prepare an inactivated vaccine.

For administration to animals, the FHV mutant according to the presentation can be given inter alia intranasally, intradermally, subcutaneously or intramuscularly.

It is a further object of the present invention to produce subunit vaccines, pharmaceutical and diagnostic preparations comprising a heterologous polypeptide expressed by a recombinant FHV mutant according to the invention. This can be achieved by culturing cells infected with said recombinant FHV under conditions that promote expression of the heterologous polypeptide. The heterologous polypeptide may then be purified with conventional techniques to a certain extent depending on its intended use and processed further into a preparation with immunizing, therapeutic or diagnostic activity.

The above described active immunization against specific pathogens will be applied as a protective treatment in healthy animals. It goes without saying that animals already infected with a specific pathogen can be treated with antiserum comprising antibodies evoked by a recombinant FHV mutant according to the invention comprising a heterologous gene derived from the specific pathogen encoding an antigenic polypeptide. Antiserum directed against a recombinant FHV according to the invention can be prepared by immunizing animals, for example cats, with an effective amount of said recombinant FHV in order to elicit an appropriate immune response. Thereafter the animals are bled and antiserum can be prepared.

EXAMPLE 1

Characterization of a new insertion region in the unique long sequence of the FHV genome.

Preparation of FHV DNA and establishment of a genomic library in lambda vector EMBL4.

The vaccine strain of FHV-1 (commercially available as feline rhinotracheitis virus, strain G2620, from Intervet International B.V.; Holland) was grown on Crandell-Rees feline kidney (CRFK) cells (Crandell, R. A. et al., In Vitro 9, 176–185, 1973) in Glasgow's modified minimum essential medium supplemented with 2.0 g/l tryptose, 2.5 g/l lactalbumin hydrolysate and 5% foetal calf serum. Culture supernatants were harvested after full cytopathic effect had developed and virus was concentrated by precipitation with polyethylene glycol (Yamamoto, K. R. et al., Virology 40, 734–744, 1970). DNA was released from virus particles by digestion at 37° C. for two hours with 100 µg/ml proteinase K (Promega, Wis., USA) in a buffer containing 20 mM Tris-HCl (pH 7.5), 10 mM EDTA and 0.5% SDS. After repeated extractions with a 1:1 mixture of phenol/chloroform, nucleic acids were precipitated with two volumes of ethanol and dissolved in TE (10 mM Tris-HCl, pH 7.5, 1 mM EDTA). Viral DNA was partially digested with the restriction enzyme Sau3A (Promega, Wis., USA) according to the conditions recommended by the enzyme supplier and reaction products were separated on a preparative 0.8% agarose gel. Fragments of the size fraction between 10 and 15 kb were isolated and ligated 2 hours at 15° C. with DNA from bacteriophage lambda EMBL4 digested with BamHI and SalI (Kaiser, K. and Murray, N. in "DNA Cloning", Volume 1, Chapter 1, IRL Press, 1985). Reaction products were packaged in vitro (Promega, Wis., USA) and recombinant phage was plated on E. coli host strain LE392. The library in lambda EMBL4 was enriched for recombinants containing inserts with sequences specifically present in relatively large SalI restriction fragments of the viral genome by screening nitrocellulose replica filters with a $^{32}$P-labelled DNA probe consisting of 10–15 kb restriction fragments isolated by preparative agarose gel electroforesis of FHV genomic DNA digested with SalI (for technical details see Sambrook, J. et al., in "Molecular Cloning: A laboratory manual", Chapter 2, Cold Spring Harbor Laboratory Press, 1989). Individual recombinants obtained from this screening procedure were amplified and the restriction pattern of the lambda insert DNA were compared with the published map of the complete FHV genome (Grail, A. et al., Arch. Virol., 116, 209–220, 1991). One of the isolates designated λFHV02, was selected for further study and the 10.9 kb insert of this clone (see FIG. 1) was positioned near the left end of the unique long segment of the viral genome between unit 0.08 and 0.17 on the map of Grail et al., supra.

Insertion of a marker gene

Figure 2A:
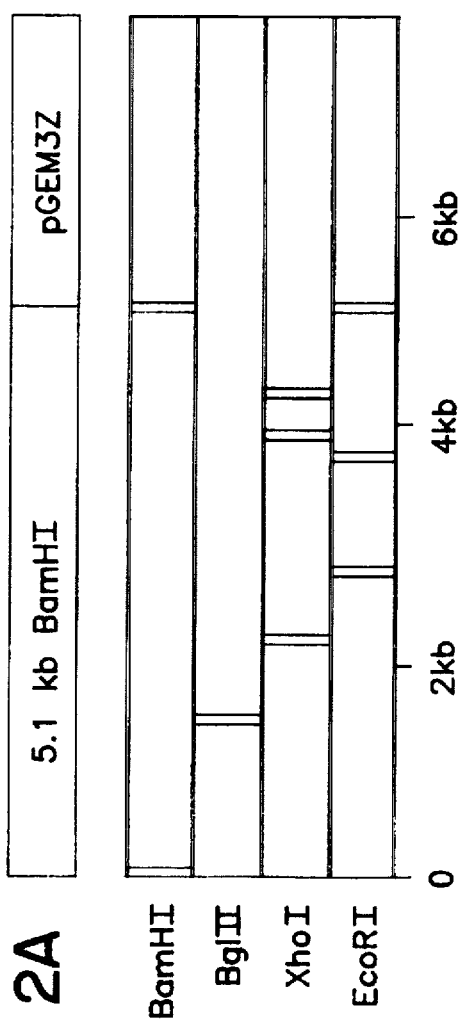

The 5.1 kb BamHI fragment of λFHV02 which was subcloned in pGEM3Z resulting in pFHV01 (see FIG. 2A), revealed a unique BglII restriction site in a suitable position for the integration of a marker gene. The gene used for insertion was derived from pCH110 (Pharmacia, Uppsala, Sweden) by replacing a 72 bp SphI fragment near the SV40 origin of replication as present in pCH110 by a double stranded synthetic oligonucleotide with the following structure (SEQ ID No.: 3 and 4):

```
5' - GGATCCGTCGACCATG- 3'
3' - GTACCCTAGGCAGCTG- 5'
```

Figure 2B:
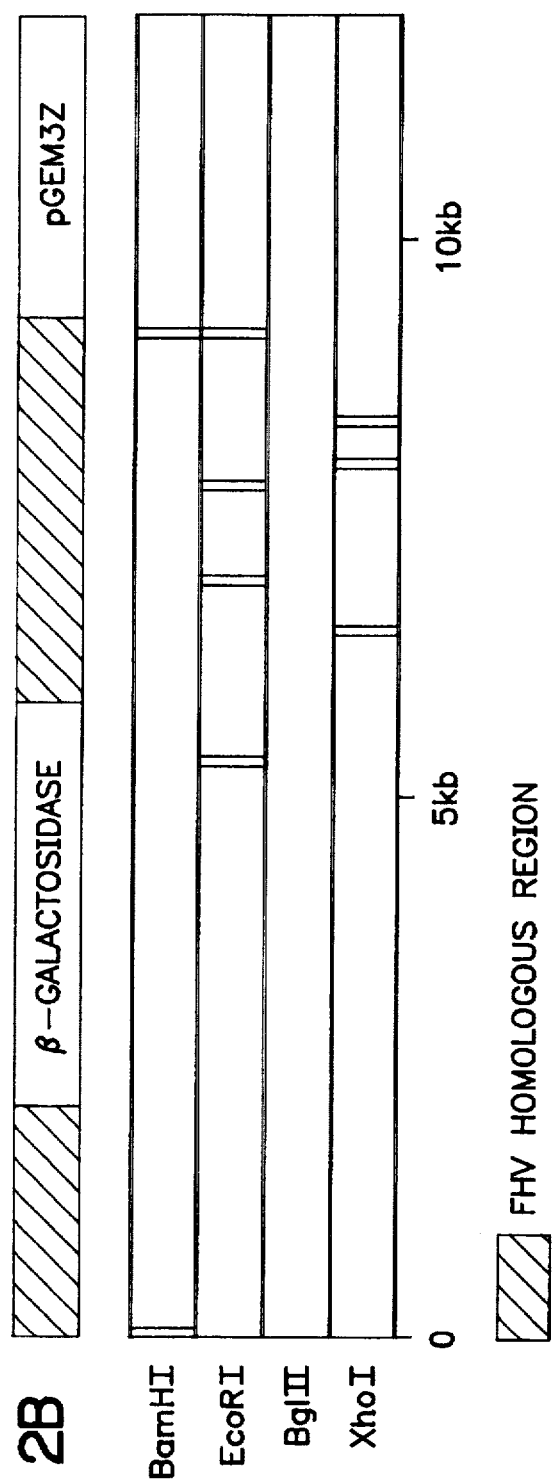
Figure 3A:
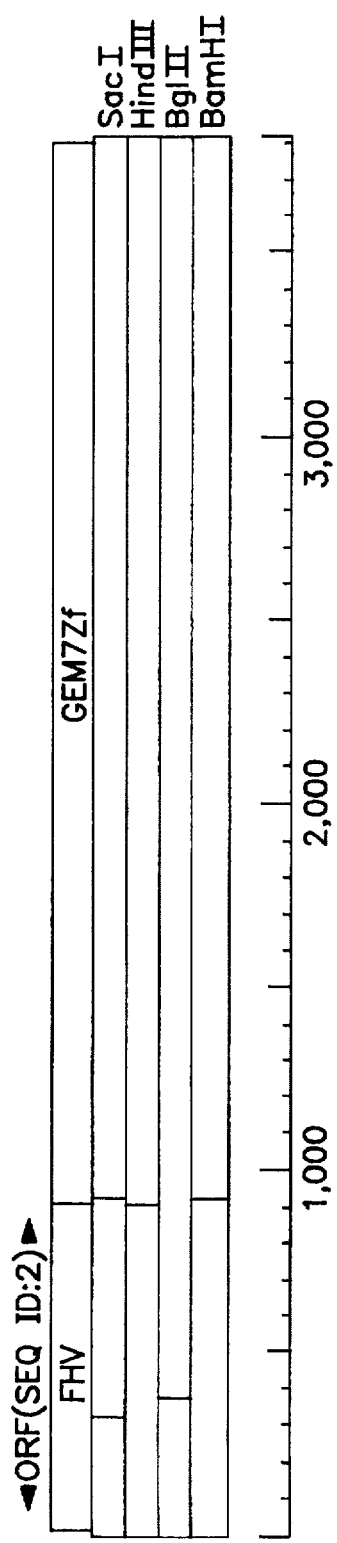
Figure 3B:
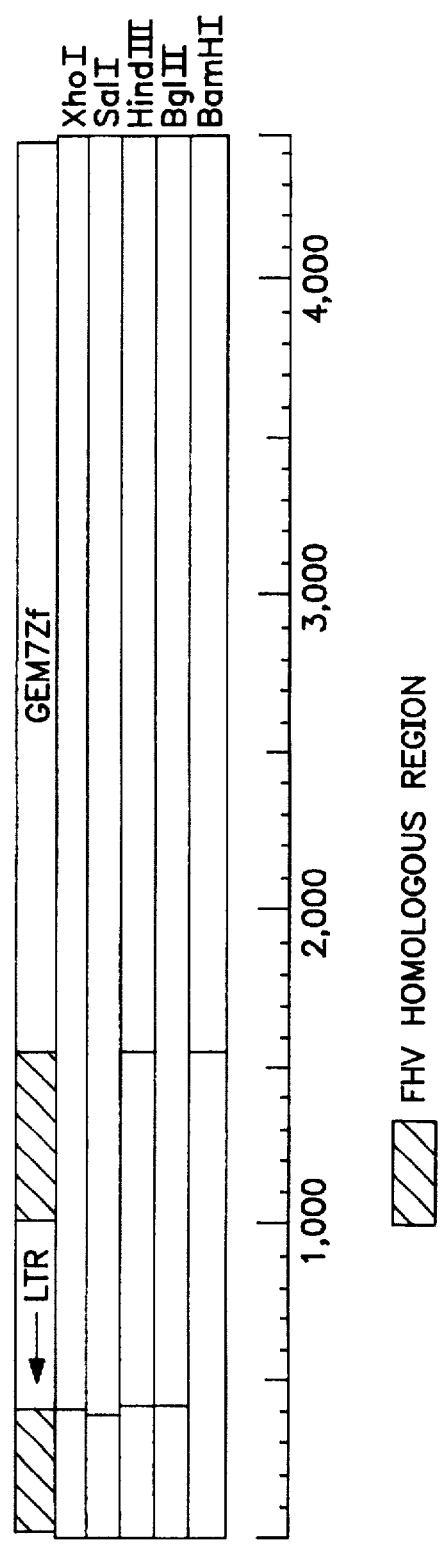

Insertion of the linker between the two SphI restriction sites of pCH110 does not restore the recognition sequence for SphI on either site and creates both a BamHI and SalI site upstream of the SV40 early promotor. Subsequent digestion with BamHI generated a 4.0 kb β-galactosidase expression cassette which was inserted at the BglII site of pFHV01 resulting in pFHV04 (see FIG. 2B). Linearized DNA of plasmid pFHV04 was introduced together with viral DNA into CRFK cells by calciumphosphate-mediated DNA precipitation (Graham, F. L. and v. d. Eb, A. J., Virology 52, 456–467, 1973). One microgram of DNA from pFHV04 were mixed with 15 microgram of DNA from FHV infected cells in a final volume of 376 μl H₂O and added to 500 μl of 2×HBSP (10 mM KCl, 280 mM NaCl, 12 mM glucose, 1.5 mM Na₂HPO₄, 50 mM HEPES, pH 7.0). Precipitates were formed by gradually adding 124 μl of 1M CaCl₂ solution and incubating the mixtures at room-temperature for 30 minutes. The suspension of precipitated DNA was gently added to two φ6 cm dishes containing each a semiconfluent monolayer of CRFK cells in 5 ml of culture medium. After 5 hours, medium was removed and 5 ml of HBSP with 15% glycerol was layered onto the cells. After a one to two minute incubation, the solution was removed, cells were washed with medium and dishes were incubated with overlayers of 0.75% agarose in culture medium. After 3 to 4 days when cytopathic effect started to develop, a second agarose overlay containing the substrate Bluogal (Gibco-BRL, Maryland, USA) with a final concentration of 0.2 mg/ml, was added and plates were incubated until blue plaques were detected. Positive plaques were picked macroscopically and transferred to flasks with fresh CRFK cells in order to amplify the virus. The plating procedure and plaque isolation was continued until homogeneous stocks of recombinant virus had been established. Virus material from the final preparations was used for detailed analysis of the viral genome by Southern blotting and for animal vaccination experiments. Recombinant FHV containing the β-galactosidase marker gene inserted at the BglII site as present in pFHV01, was shown to be stable upon serial passage in tissue culture on CRFK cells.

Structural analysis of the insertion region in the unique long segment of the FHV genome.

The nucleotide sequence analysis was performed on relevant parts of the 5.1 kb BamHI fragment present in pFHV01. The same fragment was thereto subcloned in both orientations into the BglII site of pSP72 (Promega, Wis., USA) resulting in pFHV02 and pFHV03 respectively. Progressive deletions were introduced using the enzyme exonuclease III (Henikoff, S., Gene 28, 351–359, 1984) after double digestion of the plasmid DNA with the appropriate restriction enzymes creating a 5'- and 3'-overhanging extremity. The presence of a 3'-overhanging single strand extremity prevented the plasmid vector DNA from being degraded by exonuclease III. Samples of the reaction mixture were taken at 30 seconds intervals and treated according to Henikoff supra., generating recirculatized DNA molecules which were transformed into competent *E. coli* cells. Plasmid DNA from mini-preparations of individual colonies were analyzed by restriction mapping for the size of the deletion introduced in the original 5.1 kb fragment. Series of candidates containing progressive deletions were analyzed by nucleotide sequencing on double stranded DNA in a chain termination reaction using T7 polymerase (Pharmacia, Uppsala, Sweden). Incomplete or ambiguous readings within the nucleotide sequence were resolved by specific priming of the chain elongation reaction on the inserted DNA of plasmid pFHV01, pFHV02 or pFHV03. Sequence data were assembled and analyzed using Gene-Master (Bio-Rad, California, USA) or equivalent software. Assemblage of all data resulted in an about 1.0 kb region (SEQ ID NO: 1) within the unique long segment of the FHV genome consisting of a 579 nucleotide open reading frame encoding a polypeptide with an amino acid sequence shown in SEQ ID NO:2 containing the actual BglII restriction site used for the insertion of a marker gene and about 0.4 kb of non-translated flanking DNA sequence. The region of about 1.0 kb can be applied for the insertion of foreign genes into the genome of FHV without disabling essential viral functions necessary for infection and replication.

EXAMPLE 2

Construction of recombinant FHV expressing the envelope protein from feline leukemia virus (FeLV)

Based on the sequence as presented in SEQ ID: 1, a fragment was derived from pFHV02 by trimming both ends of the 5.1 kb BamHI insert using the enzyme exonuclease III and following similar procedures as described for the nucleotide sequence analysis. This resulted in pFHV24 containing a 0.9 kb insert in pGEM7Zf(+) (Promega, Wis., USA) with the unique BglII restriction site previously defined in pFHV01 correctly positioned for the integration of foreign DNA and subsequent in vivo recombination with the viral genome (see FIG. 3A). A strong promotor which could direct the expression of foreign genes after their insertion into the genome of the FHV virus was selected from the LTR sequence of Rous sarcoma virus, (RSV).

The promotor has been mapped on a 580 bp NdeI/HindIII restriction fragment from pRSVcat (Gorman, C. M. et al., Proc. Natl. Acad. Sci. USA 79, 6777–6781, 1982) and was inserted between the HindIII and PstI sites of pGEM3Z by means of double stranded synthetic linkers on both sides of the fragment. The connection between the HindIII site from the vector pGEM3Z and the NdeI site of the RSV fragment carrying the LTR promotor was made with a 30 bp linker containing cohesive ends compatible with HindIII on one and NdeI on the other site. However, after ligation both restriction sites are not restored due to deliberate modifications in the outer nucleotides of the six basepair recognition sequence. In addition to the removal of these two sites, a new restriction site (BamHI) present within the linker itself was created at the corresponding position. A second 20 bp linker was synthesized which connected the HindIII site from the LTR fragment to the PstI site from pGEM3Z, in this case without destruction of the recognition sequence on either of the ends and adding the convenient unique restriction sites BglII and XhoI, to those already present in the polylinker of pGEM3Z, e.g. PstI, XbaI and BamHI. The resulting derivative of pGEM3Z, designated pVEC01, therefore contains a 650 bp restriction fragment carrying the LTR promotor sequence immediately followed by multiple restriction sites available for the insertion of foreign genes. The 650 bp fragment is flanked on either end by a BamHI restriction site and has been transferred as such to the unique BglII site present in pFHV24. The cohesive ends generated by these two restriction enzymes enzymes are compatible but ligation does not restore either of the original recognition sequences for BglII or BamHI. One of the resulting constructs was designated pFHV28 and checked by restriction mapping (FIG. 3B). The structure of this FHV recombination vector allows the insertion of foreign genes immediately downstream the LTR promotor and subsequent integration of the complete expression cassette into the FHV genome by in vivo recombination. The positions of the different restriction sites downstream of the LTR in particular those for the enzymes BglII and XhoI, are designed in such a way that even multiple gene insertion can be envisaged. A first application of this vector consisted of the gene encoding the envelope protein from FeLV/sub-group A and was isolated on a 2.0 kb PstI fragment from pFGA-5 (Stewart, M. A., et al., J. Virol. 58, 825–834, 1986) and subcloned with the coding strand in the T7-orientation of pGEM3Z. The unique SphI site present in the polylinker of the vector was replaced by BamHI through the addition of a synthetic linker similar to the modification introduced in pCH110 (see example 1).

Figure 4:
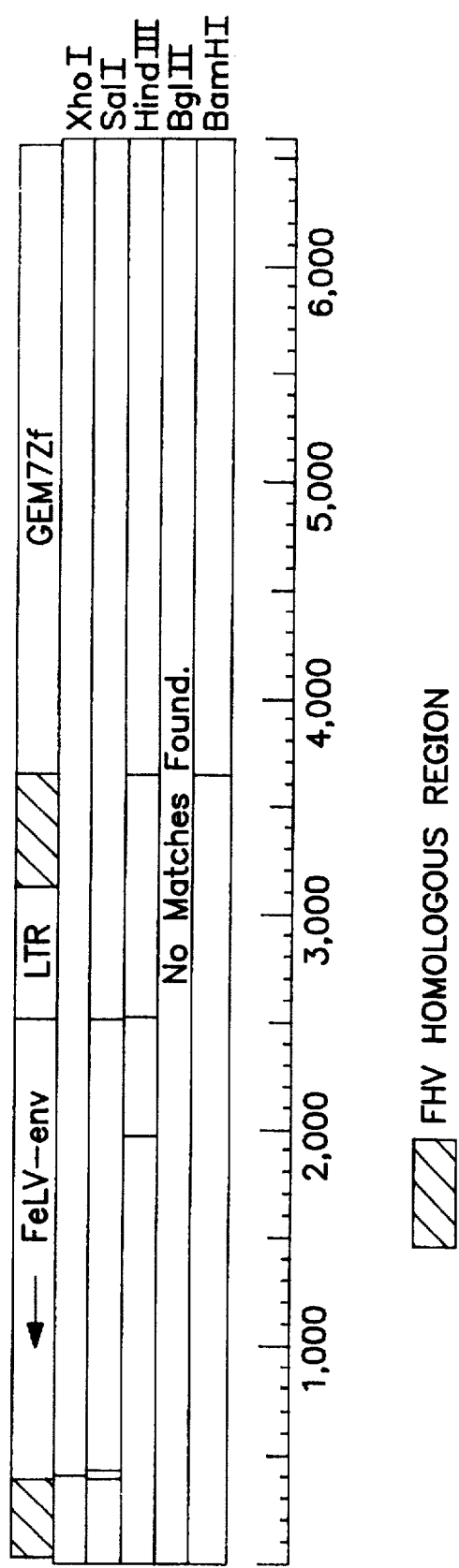

The complete gene which could now be isolated on a 2.0 kb BamHI fragment, was inserted at the BglII site of pFHV28 resulting in pFHV29. The correct orientation of the FeLV envelope gene relative to the LTR promotor was confirmed by restriction analysis (see FIG. 4). One microgram of linearized DNA of plasmid pFHV29 was cotransfected with 15 microgram of viral DNA into CRFK cells as described previously in example 1 for the insertion of the β-galactosidase marker gene. The transfection progeny was harvested after 3 to 4 days and seeded in serial dilutions onto CRFK cells in microtiter plates. After cpe had developed, plates were fixed with ethanol and incubated with a rabbit antibody raised against the purified native envelope protein of FeLV. Specifically bound antibodies were detected with a fluorescein-labelled goat anti-rabbit serum and visualized under a UV-microscope. Plaques harbouring recombinant FHV and expressing the envelope protein of FeLV were detected at a frequence of about $5 \times 10^{-4}$.

EXAMPLE 3

Construction of recombinant FHV expressing the envelope protein from feline immunodeficiency virus (FIV)

Figure 5:
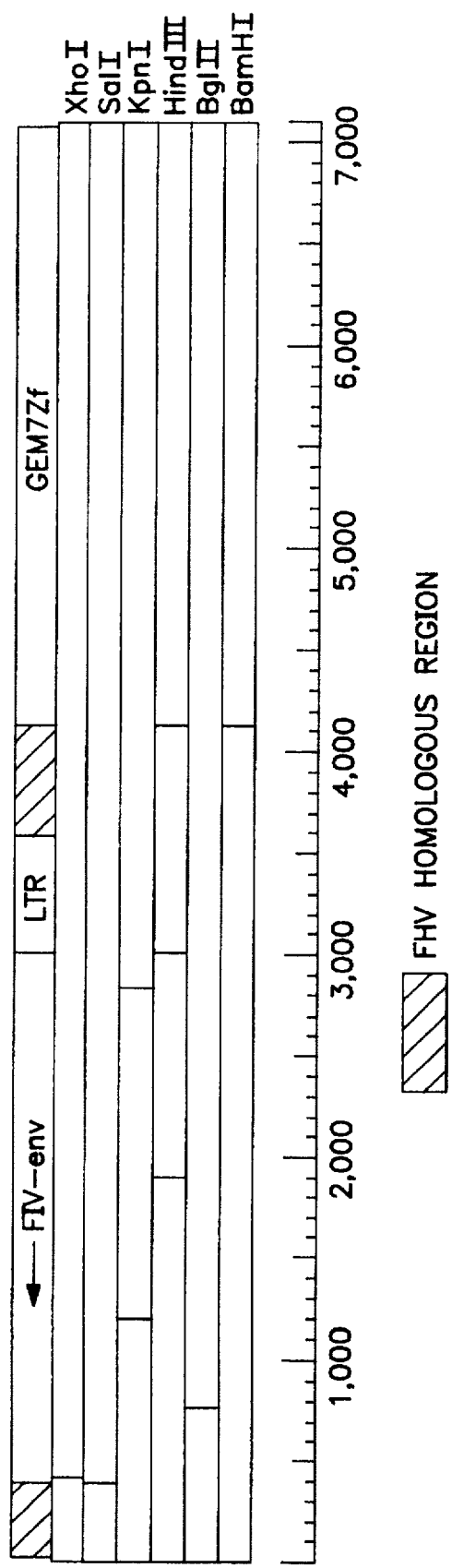

The gene encoding the envelope protein from FIV was also considered as an important candidate to be inserted into the specific region of the $U_l$ from FHV. The gene was derived from the proviral genome of a Dutch FIV isolate referred to as FIV-UT 113 (Verschoor, E. J. et al., Virology 193, 433–438, 1993) and subcloned as a 2.6 kb BamHI fragment before insertion into the BglII site of pFHV 28 similar to the procedures as described above for the envelope gene of FeLV. The resulting recombination plasmid pFHV 37 (see FIG. 5) was transfected together with FHV viral DNA into CRFK cells as has been described in example 1 for the β-galactosidase expression cassette. The viral progeny of the transfection was seeded on CRFK cells in microtiter plates such that about 50 to 100 pfu per well were obtained. After incubation, the supernatant of each individual well was stored separately and the remainder of the plates was fixed with ethanol. Plates were incubated with the primary reagent consisting of a serum from FIV infected cats. Envelope specific antibodies were detected with a fluorescein-labelled rabbit anti-cat serum and microscopically visualized under UV light. Wells harbouring positive foci were scored and the corresponding virus samples which had been stored in parallel were seeded again in limiting dilutions of about 1 to 5 pfu per well and treated in a similar way as described above. The plating procedure was repeated until the virus stock appeared to be more than 50% homogeneous for the expression of the envelope protein as detected in an immuno fluorescence assay. A final purification was performed by single-plaque isolation under an agarose overlay. One of the isolates obtained by this procedure was selected and designated FHV strain F2-1. Amplified stocks with titers of more than $1 \times 10^7$ pfu/ml were prepared on CRFK cells and frozen at $-80°$ C. until further experimentation.

The viral genome structure of strain F2-1 was analyzed by Southern blotting using a DNA fragment containing the LTR promotor as a probe in the hybridization. The position of BglII and EcoRI restriction sites in the region of the genome where the envelope gene was inserted was found to be consistent with the expected pattern.

EXAMPLE 4

Pathogenicity of FHV mutant in infected animals

One of the recombinant viruses constructed as described above in example 1 and containing the β-galactosidase gene inserted at the BglII site present within the 1 kb region of the unique long segment as defined in SEQ ID No.: 1, was designated FHV strain 05-4-1-1. The pathogenicity of this virus and the ability to protect against the clinical signs caused by challenge with a virulent FHV strain was studied in an animal experiment and compared with the parent strain G2620.

Specific pathogen-free cats 12 weeks of age were infected oronasally with ca. $1 \times 10^5$ TCID$_{50}$ of the FHV-1 mutant or parent strain by applying 0.3 ml per nostril and 0.4 ml in the oropharynx. Animals were observed daily over a period of 2 weeks for clinical signs specific for FHV-1 infection and scored based on the criteria as listed in Table 1. Cats were challenged six weeks after vaccination by oronasal application of $1 \times 10^5$ TCID$_{50}$ of FHV-1 strain SGE (National Veterinary Service Laboratory, USA) and monitored over a period of 2 weeks for clinical signs of FHV-1 infection. Clinical observations both after vaccination and challenge are summarized in Table 2. Cats in group one that had received an oronasal vaccination with strain 05-4-1-1 showed a reduced level in the score for clinical signs compared to the animals in group two receiving the parent G2620 strain.

After challenge, the vaccinated cats in group 1 and 2 showed an average 10-fold reduction in the clinical scores compared to the non-vaccinated controls in group 3. Therefore it was concluded that the mutant strain 05-4-1-1 had a reduced virulence upon oronasal application in the cat and was still capable of inducing high levels of protection against the clinical signs of a challenge FHV infection.

TABLE 1

| Clin. sign | Severity | Daily Score (points) |
|---|---|---|
| Pyrexia | >39.6–39.9 | 1 |
| | 40.0–40.4 | 2 |
| | 40.5–40.9 | 3 |
| | >41.0 | 4 |
| Sneezing | infrequent | 1 |
| | frequent | 2 |
| | paroxysmal | 3 |
| Cough | infrequent | 1 |
| | frequent | 2 |
| Respiration | URT noise | 1 |
| | stertor | 1 |
| | mouth breathing | 2 |
| Salivation | | 2 |
| Conjunctivitis | mild | 1 per eye |
| | moderate | 2 per eye |
| | severe | 3 per eye |
| Ocular discharge | serous | 1 per eye |
| | mucopurulent | 2 per eye |
| Nasal discharge | serous | 1 per nostril |
| | mucopurulent | 2 per nostril |
| Ulceration | nasal | 2 |
| | nasal/bleeding | 3 |
| | oral | 2 |
| | oral/bleeding | 3 |
| Oral erythema | | 1 |
| Inappetance | | 1 |
| Depression | | 1 |

TABLE 2

| Group | Vaccine | animal code | clin. scores after vaccination | | clin. scores after challenge | |
|---|---|---|---|---|---|---|
| | | | individual scores | average | individual scores | average |
| 1 | 05-4-1-1 | 40L | 2 | | 2 | |
| | | 40M | 0 | | 7 | |
| | | 40P | 0 | 0.5 | 10 | 7.3 |
| | | 40R | 0 | | 10 | |
| 2 | G2620 | 40V | 1 | | 1 | |
| | | 40W | 8 | | 7 | |
| | | 40X | 5 | 7.0 | 6 | 5.5 |
| | | H18 | 14 | | 8 | |
| 3 | none | H14 | — | | 77 | |
| | | H12 | — | | 85 | |
| | | H11 | — | — | 69 | 79.7 |
| | | B39 | — | | 88 | |

We claim:

1. A method for the immunization of animals against an infectious disease, comprising administering a vaccine comprising an FHV mutant, said FHV mutant comprising a mutation in the DNA of an open reading frame that encodes the polypeptide shown in SEQ ID NO:2, and/or flanking intergenic sequences thereof, such that the FHV mutant does not produce a functional polypeptide coded for by said open reading frame.

2. The method according to claim 1, wherein the mutant comprises a heterologous nucleic acid sequences, which is inserted into said open reading frame and/or flanking intergenic sequences thereof.

3. The method according to claim 2, wherein the heterologous nucleic acid sequence is inserted into said open reading frame.

4. The method according to claim 3, wherein the heterologous nucleic acid sequence is inserted at a BGlII restriction site in said open reading frame.

5. The method according to claim 1, wherein only part of the FHV DNA within said open reading frame is deleted.

6. The method according to claim 2, wherein the heterologous nucleic acid sequence encodes a heterologous polypeptide and is under the control of a promoter regulating the expression of said polypeptide in a cell infected with the FHV mutant.

7. The method according to claim 6, wherein the heterologous nucleic acid sequence encodes an antigen of a feline pathogen.

8. The method according to claim 7, wherein the pathogen is selected from the group consisting of feline leukemia virus, feline immunodeficiency virus, feline calicivirus, feline parvovirus, feline coronavirus and feline chlamydia.

9. A method for the immunization of animals against an infectious disease, comprising administering a vaccine comprising a feline herpesvirus (FHV) mutant having a mutation in the DNA of an open reading frame having the nucleotide sequence shown in SEQ ID NO: 1 and/or flanking intergenic sequences thereof, wherein the FHV mutant does not produce a functional polypeptide from said open reading frame.

10. The method according to claim 9, wherein the mutant comprises a heterologous nucleic acid sequence that is inserted into said open reading frame and/or flanking intergenic sequences thereof.

11. The method according to claim 10, wherein the heterologous nucleic acid sequence is inserted at a BGlII restriction site in the open reading frame.

12. The method according to claim 10, wherein only a part of the FHV DNA sequence within the open reading frame is deleted.

13. The FHV mutant according to claim 10, wherein the heterologous nucleic acid sequence encodes a heterologous polypeptide and is under the control of a promoter regulating the expression of said polypeptide in a cell infected with the FHV mutant.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1007 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Feline herpesvirus (FHV-1)
        ( B ) STRAIN: G 2620

( v i i ) IMMEDIATE SOURCE:
        ( B ) CLONE: pFHV01

( i x ) FEATURE:
        ( A ) NAME/KEY: CDS
        ( B ) LOCATION: 253..834

( x i ) SEQUENCE DESCRIPTION: SEQ ID NO:1:

```
TAACTCTTAT AGTTCGTATA AATTACTTAT CATAACCGTG TTTCAGCGGT TATATTTTTA      60

TAACAGTTAA TTGTTTACTA ATAGTTTACA AAGTCCATCG TTTATAAAAA ACAAGCCCAG     120

TGGTATTATA ATCATTCGTA TGGATATAAA CCGACTCCAA TCCGTGATCT TTGGTAACCC     180

GCGACGTAAT TACTCTCACA CATTTTAACT AGTCTACGAT CACCCAGATA TAATAAAAAG     240

ATTCGCGTGG AC ATG CAA GGT ATG AGG TCT ACG TCA CAG CCG TTG GTC         288
              Met Gln Gly Met Arg Ser Thr Ser Gln Pro Leu Val
               1               5                  10

GAG ATA CCA CTG GTA GAT ATG GAA CCA CAG CCA TCT ATA CAC TCC AAC      336
Glu Ile Pro Leu Val Asp Met Glu Pro Gln Pro Ser Ile His Ser Asn
         15                  20                  25

GAG CCT AAC CCA CCG AAT AAA ATG TTG ACG ACA GCT ATT TCA TCG CGT      384
Glu Pro Asn Pro Pro Asn Lys Met Leu Thr Thr Ala Ile Ser Ser Arg
     30                  35                  40

AGG AGT GGA ATT TTT TTA TTT TCT CTG GGT ATG TTT TTT TTC GGA GTT      432
Arg Ser Gly Ile Phe Leu Phe Ser Leu Gly Met Phe Phe Phe Gly Val
 45                  50                  55                  60

ATC CTA ACA GCT ACT ATT ATA GTA TGT ACA TTC ATA TTT ACA ATA CCA      480
Ile Leu Thr Ala Thr Ile Ile Val Cys Thr Phe Ile Phe Thr Ile Pro
                 65                  70                  75
```

-continued

```
GTG GAT ATG CTC CAG ATG CCA CGC TGC CCT GAG GAA ACG GTG GGT ATC        528
Val Asp Met Leu Gln Met Pro Arg Cys Pro Glu Glu Thr Val Gly Ile
        80                      85                      90

AAA AAC TGT TGT ATC CGA CCG ATT AGA CGC CAT GTT AAA TCA CAC CAA        576
Lys Asn Cys Cys Ile Arg Pro Ile Arg Arg His Val Lys Ser His Gln
            95                     100                    105

GAT CTA GTT GCC ACA TGT GCC GAA TAC ATG GAA CAA CCC GCC ACC GCA        624
Asp Leu Val Ala Thr Cys Ala Glu Tyr Met Glu Gln Pro Ala Thr Ala
    110                     115                     120

TCT GCT GTT GGA GCT CTT ATA CCA TTA TTG GAC ATC TTC AAT GGA GAT        672
Ser Ala Val Gly Ala Leu Ile Pro Leu Leu Asp Ile Phe Asn Gly Asp
125                     130                     135                 140

GGG ATA TCT ACA AAC GAC TCT CTT TAC GAT TGT ATT CTC TCT GAT GAA        720
Gly Ile Ser Thr Asn Asp Ser Leu Tyr Asp Cys Ile Leu Ser Asp Glu
                    145                     150                     155

AAA AAA TCG TGT AAT ACA TCA ATG GCC GTA TGT CAA TCA ACA TAT CTT        768
Lys Lys Ser Cys Asn Thr Ser Met Ala Val Cys Gln Ser Thr Tyr Leu
            160                     165                     170

CCA AAT CCC CTA AGT GAC TTT ATT ATG CGC GTT AGG CAG ATA TTT TCT        816
Pro Asn Pro Leu Ser Asp Phe Ile Met Arg Val Arg Gln Ile Phe Ser
    175                     180                     185

GGA ATC CTA AAT CAT TAATCCATTT ACTAAATAAA TAAACAATAC CGTTTAGGTA        871
Gly Ile Leu Asn His
190

ATTAAACATG ATTCTAGTGT TTATTGTCGT ATGTACGGGC GATGGTTGGA TAACAACTCG      931

ACAATGATCA ATTATATTGA TTAACCTTGT AATAAATTCG TCGGATTATT GGATATATCG      991

AGATGATATC ACATTA                                                     1007
```

( 2 ) INFORMATION FOR SEQ ID NO:2:

( i ) SEQUENCE CHARACTERISTICS:
        ( A ) LENGTH: 193 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Gly Met Arg Ser Thr Ser Gln Pro Leu Val Glu Ile Pro Leu
 1               5                  10                  15

Val Asp Met Glu Pro Gln Pro Ser Ile His Ser Asn Glu Pro Asn Pro
            20                  25                  30

Pro Asn Lys Met Leu Thr Thr Ala Ile Ser Ser Arg Arg Ser Gly Ile
        35                  40                  45

Phe Leu Phe Ser Leu Gly Met Phe Phe Phe Gly Val Ile Leu Thr Ala
    50                  55                  60

Thr Ile Ile Val Cys Thr Phe Ile Phe Thr Ile Pro Val Asp Met Leu
65                  70                  75                  80

Gln Met Pro Arg Cys Pro Glu Glu Thr Val Gly Ile Lys Asn Cys Cys
                85                  90                  95

Ile Arg Pro Ile Arg Arg His Val Lys Ser His Gln Asp Leu Val Ala
            100                 105                 110

Thr Cys Ala Glu Tyr Met Glu Gln Pro Ala Thr Ala Ser Ala Val Gly
        115                 120                 125

Ala Leu Ile Pro Leu Leu Asp Ile Phe Asn Gly Asp Gly Ile Ser Thr
    130                 135                 140

Asn Asp Ser Leu Tyr Asp Cys Ile Leu Ser Asp Glu Lys Lys Ser Cys
145                 150                 155                 160
```

```
Asn Thr Ser Met Ala Val Cys Gln Ser Thr Tyr Leu Pro Asn Pro Leu
            165                 170                 175

Ser Asp Phe Ile Met Arg Val Arg Gln Ile Phe Ser Gly Ile Leu Asn
            180                 185                 190

His
```

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..16
        ( D ) OTHER INFORMATION: /label=linker_1

( x i ) SEQUENCE DESCRIPTION: SEQ ID NO:3:

GGATCCGTCG ACCATG     16

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..16
        ( D ) OTHER INFORMATION: /label=linker_2

( x i ) SEQUENCE DESCRIPTION: SEQ ID NO:4:

GTACCCTAGG CAGCTG     16